United States Patent [19]

Large et al.

[11] 4,004,001
[45] Jan. 18, 1977

[54] PHOSPHORUS CONTAINING INSECTICIDE ACTIVATORS

[75] Inventors: George B. Large, Orinda; Leland S. Pitt, San Jose, both of Calif.

[73] Assignee: Stauffer Chemical Company, Westport, Conn.

[22] Filed: Sept. 2, 1975

[21] Appl. No.: 609,865

Related U.S. Application Data

[63] Continuation-in-part of Ser. No. 433,182, Jan. 14, 1974, abandoned.

[52] U.S. Cl. .............................. 424/200; 424/203; 424/225; 260/945; 260/951; 260/963; 260/964
[51] Int. Cl.$^2$ ............................................ A01N 9/36
[58] Field of Search .......... 424/200, 224; 260/945, 260/951, 964

[56] References Cited

UNITED STATES PATENTS

| | | | |
|---|---|---|---|
| 2,767,194 | 10/1956 | Fancher | 424/200 |
| 2,770,567 | 11/1956 | Wedemeyer et al. | 424/224 |
| 3,193,452 | 7/1965 | Jager et al. | 424/200 |
| 3,743,728 | 7/1973 | Fancher | 424/200 |

*Primary Examiner*—V. D. Turner
*Attorney, Agent, or Firm*—Daniel C. Block

[57] ABSTRACT

A composition of matter is described herein which is useful as an activator for insecticides. The activator composition is defined by the formula

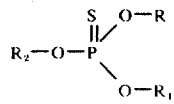

wherein R is selected from the group consisting of methyl, ethyl, n-propyl, i-propyl and i-butyl; $R_1$ is selected from the group consisting of methyl, ethyl, n-propyl, i-propyl, n-butyl, and i-butyl; $R_2$ is selected from the group consisting of phenyl, substituted phenyl wherein said substituents are selected from methyl, ethyl, i-propyl, t-butyl, methoxy, ethoxy and dimethylamino; phenalkyl and substituted phenalkyl wherein said substituents are selected from chlorine, methyl, i-propyl and methoxy.

41 Claims, No Drawings

PHOSPHORUS CONTAINING INSECTICIDE ACTIVATORS

CROSS REFERENCE TO RELATED APPLICATION

This application is a continuation-in-part of copending application Ser. No. 433,182, filed Jan. 14, 1974, now abandoned.

BACKGROUND OF THE INVENTION

Among the many insecticidal compounds, the phthalimidiothiophosphates have reached a relatively high degree of commercial success. These compounds are toxic to a large number of insect pests at different concentrations varying with the resistance of the insects mentioned. Some of these compounds are described in U.S. Pat. No. 2,767,194, specifically N-(mercaptomethyl) phthalimide-S-(O,O-dimethylphosphorodithioate).

The endeavor to extend the usefulness of the thiophosphates by increasing their effectiveness and lowering the cost has led to extensive studies on another class of biologically active chemicals, customarily referred to as synergists. Among the many synergists employed, the alkyl oxides, specifically, piperonyl butoxide, have been widely used. These compounds are described in U.S. Pat. No. 2,485,681 and 2,550,737.

DETAILED DESCRIPTION OF THE INVENTION

It has been discovered that the thiophosphate compounds having insecticidal activity can be increased by using an activator having the formula

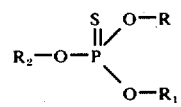

wherein R is selected from the group consisting of methyl, ethyl, n-propyl, i-propyl and i-butyl; $R_1$ is selected from the group consisting of methyl, ethyl, n-propyl, i-propyl and i-butyl; $R_2$ is selected from the group consisting of phenyl, substituted phenyl wherein said substituents are selected from methyl, ethyl, i-propyl, t-butyl, methoxy, ethoxy and dimethylamino; phenalkyl and substituted phenalkyl wherein said substituents are selected from chlorine, methyl, i-propyl and methoxy.

These compounds are manufactured by reacting an appropriate phenol or phenalkyl compound with certain haloalkyl phosphoro derivatives. After the end products are achieved, they are isolated and purified and admixed with the insecticidal compound. The amount of activator admixed therewith can range between about 1 to 0.1 to about 1 to 10 parts insecticidal compound to activator compound. After the insecticidal compound and activator compound are mixed together, they are applied to the habitat of the insect in a conventional manner.

In order to illustrate the merits of the present invention, the following examples are provided:

EXAMPLE 1

O,O-Dimethyl-O-phenyl phosphorothioate

To a solution of 9.4 grams (0.1 mole) phenol in 100 ml tetrahydrofuran was added 4.4 grams (0.11 mole) powered NaOH stirred until clear. A solution of 16.0 grams (0.1 mole) O,O-dimethyl phosphorochloridothioate in 25 ml tetrahydrofuran was added slowly to the sodium phenylate solution and refluxed for 30 minutes. Benzene (100 ml) was added to the mixture. The resulting mixture was washed with 10% NaOH and twice with $H_2O$, dried over anhydrous $MgSO_4$ and the volitiles removed under reduced pressure to yield 20.2 grams $N_D^{30}$ 1.5327.

EXAMPLE 2

O,O-Diethyl-O-phenyl phosphorothioate

The procedure of Example 1 was repeated, except 18.9 grams (0.1 mole) of O,O-diethyl phosphorochloridothioate was used. The yield was 24.6 grams $N_D^{30}$ 1.5077.

Additional compounds were synthesized in a similar manner using appropriate starting materials. These compounds are listed in the following table.

TABLE I

| Compound Number | R | $R_1$ | $R_2$ |
| --- | --- | --- | --- |
| 1 | —$CH_3$ | —$CH_3$ |  |
| 2 | —$CH_3$ | —$CH_3$ | 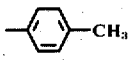 (CH₃) |
| 3 | —$CH_3$ | —$CH_3$ | 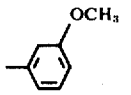—$CH_3$ |
| 4 | —$CH_3$ | —$CH_3$ | 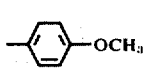 ($OCH_3$) |
| 5 | —$CH_3$ | —$CH_3$ | —⟨⟩—$OCH_3$ |

TABLE I-continued $$R_2-O-\overset{\overset{S}{\|}}{\underset{O-R_1}{P}}-O-R$$

| Compound Number | R | $R_1$ | $R_2$ |
|---|---|---|---|
| 6 | —CH₃ | —CH₃ | 2-ethoxyphenyl (OC₂H₅ on phenyl) |
| 7 | —CH₃ | —CH₃ | 4-isopropylphenyl |
| 8 | —CH₃ | —CH₃ | 2-tert-butylphenyl |
| 9 | —CH₃ | —CH₃ | 3-tert-butylphenyl |
| 10 | —CH₃ | —CH₃ | 3-(N,N-dimethylamino)phenyl |
| 11 | —CH₃ | —CH₃ | 2-methoxy-5-methylphenyl |
| 12 | —CH₃ | —CH₃ | 2,3-dimethoxyphenyl |
| 13 | —CH₃ | —CH₃ | 2,5-dimethyl-N,N-dimethylaminophenyl |
| 14 | —CH₃ | —CH₃ | 2,4-diisopropyl-methylphenyl |
| 15 | —CH₂—CH(CH₃)CH₃ | —CH₂—CH(CH₃)CH₃ | —CH₂—CH₂—C₆H₅ |
| 16 | —CH(CH₃)CH₃ | —CH(CH₃)CH₃ | —CH₂—CH₂—C₆H₅ |
| 17 | —CH₃ | —CH₃ | —CH(CH₃)—C₆H₅ |
| 18 | —CH₃ | —CH₃ | —CH₂—CH₂—CH₂—C₆H₅ |

TABLE I-continued $$R-O-\underset{\underset{O-R_1}{|}}{\overset{\overset{S}{\|}}{P}}-O-R_2$$

| Compound Number | R | $R_1$ | $R_2$ |
|---|---|---|---|
| 19 | —CH₃ | —CH₃ | —CH(C₂H₅)—C₆H₅ |
| 20 | —CH₃ | —CH₃ | —CH₂—CH(CH₃)—C₆H₅ |
| 21 | —CH₃ | —CH₃ | —C(CH₃)₂—C₆H₅ |
| 22 | —C₂H₅ | —C₂H₅ | —C₆H₅ |
| 23 | —C₃H₇ | —C₃H₇ | —C₆H₅ |
| 24 | —CH(CH₃)₂ | —CH(CH₃)₂ | —C₆H₅ |
| 25 | —CH₂—CH(CH₃)₂ | —CH₂—CH(CH₃)₂ | —C₆H₅ |
| 26 | —CH₃ | —CH₃ | —CH₂—C₆H₅ |
| 27 | —CH₃ | —CH₃ | —CH₂—CH₂—C₆H₅ |
| 28 | —C₂H₅ | —C₂H₅ | —CH₂—CH₂—C₆H₅ |
| 29 | —C₃H₇ | —C₃H₇ | —CH₂—CH₂—C₆H₅ |
| 30 | —C₂H₅ | —C₂H₅ | 2,3-(CH₃)₂—C₆H₃— |
| 31 | —C₂H₅ | —C₂H₅ | 3,4-methylenedioxyphenyl |
| 32 | —C₂H₅ | —C₂H₅ | 2,3,4-(CH₃)₃—C₆H₂— |
| 33 | —C₂H₅ | —C₂H₅ | 2,3,5,6-(CH₃)₄—C₆H— |
| 34 | —C₂H₅ | —C₂H₅ | —CH₂—C₆H₅ |

TABLE I-continued $$R_2-O-P\begin{matrix}S\\\|\\\end{matrix}\begin{matrix}O-R\\O-R_1\end{matrix}$$

| Compound Number | R | $R_1$ | $R_2$ |
|---|---|---|---|
| 35 | $-C_2H_5$ | $-C_2H_5$ | $-CH_2-\text{(2-Cl-phenyl)}$ |
| 36 | $-C_2H_5$ | $-C_2H_5$ | $-CH_2-\text{(4-Cl-phenyl)}$ |
| 37 | $-C_2H_5$ | $-C_2H_5$ | $-CH_2-\text{(2,4-diCl-phenyl)}$ |
| 38 | $-C_2H_5$ | $-C_2H_5$ | $-CH_2-\text{(4-CH}_3\text{-phenyl)}$ |
| 39 | $-C_2H_5$ | $-C_2H_5$ | $-CH_2-\text{(4-iPr-phenyl)}$ |
| 40 | $-C_2H_5$ | $-C_2H_5$ | $-CH_2-\text{(2-OCH}_3\text{,4-OCH-phenyl)}$ |
| 41 | $-CH_3$ | $-C_2H_5$ | phenyl |
| 42 | $-CH_3$ | $-n-C_3H_7$ | phenyl |
| 43 | $-CH_3$ | $-n-C_4H_9$ | phenyl |
| 44 | $-C_2H_5$ | $-n-C_3H_7$ | phenyl |

Insecticidal Evaluation

A. Housefly [*Musca domestica* (L.)] (HF)

The following procedure was used to test both susceptible and S-chlorothion resistant houseflies. Stock solutions containing 100 μg/ml of the toxicant and 500 μg/ml of the activator are prepared using appropriate solvents. Toxicant and activator are combined in a 1 part toxicant: 5 parts activator ratio by adding equal aliquots of the stock solutions to one ml of a 0.2% peanut oil in acetone spreading solution in a glass Petri dish 60 mm in diameter. The toxicant/activator film residue forms in the Petri dish as the solvents evaporate. The Petri dishes are placed in a circular cardboard cage, closed on the bottom with cellophane and covered on top with cloth netting. Twenty-five female houseflies are introduced into the cage and the percent mortality is recorded after 48 hours. LD-50 values are expressed in terms of μg of toxicant per 25 female flies. The aliquots are varied to achieve desired toxicant/activator concentrations ranging from 100 μg toxicant/500 ug activator per Petri dish to that at which 50% mortality is obtained. Controls are identical to the above with the exception that the activator is omitted.

B. Black Bean Aphid [*Aphis fabae* (Scop.)] (BBA)

Nasturtium (Tropaeolum sp.) plants, approximately 2–3 inches tall, are transplanted into sandy loam soil in 3-inch clay pots and infested with 50–75 aphids of mixed ages. Twenty-four hours later they are sprayed, to the point of runoff, with aqueous suspensions of the toxicant formulated as a 50 wettable powder and activator. The suspensions are prepared in equal aliquots of the toxicant and activator dissolved in tap water and diluted in a tap water solution. Test concentrations for both toxicant and activator ranged from 0.5% to that at which 50% mortality is obtained. Mortality is recorded after 48 hours and the LD-50 values are expressed as percent active ingredient in the solutions.

C. Salt-marsh Caterpillar [*Estigmene acrea* (Drury)] (SMC)

Test solutions are prepared by dissolving equal aliquots of the toxicant and activator in a 50—50 acetone-water solution. Sections of bitter dock (*Rumex obtusifolius*) leaves, 1–1.5 inches in length are immersed in the test solutions for 1–2 seconds and placed on a wire screen to dry. The dried leaf is placed on a moistened piece of filter paper in a Petri dish and infested with five third-instar larvae. Mortality of the larvae is recorded after 48 hours and the LD-50 values are expressed as per cent toxicant in the acetone-water solutions.

D. Cabbage Looper [*Trichoplusia ni*] (CL)

Same as Salt-marsh Caterpillar (C), except that leaves of white cabbage (*Brassica oleracla*) are utilized as the host plant rather than bitter dock.

E. Tobacco Budworm [*Heliothis virescens* (F.)] (TBW)

Same as the Salt-marsh Caterpillar (C), except that leaves of Romaine lettuce (*Latuca sativa*) are utilized as the host plant rather than bitter dock.

F. Beet Armyworm [*Spodoptera exiqua* (Hubner)] (BAW)

Same as the Salt-marsh Caterpillar (C), except that leaves of Romaine lettuce (*Latuca sativa*) are utilized as the host plant rather than bitter dock.

Activating Factor

The Activating Factor is arrived at by using the following formula from the expected response for a given combination of two insecticides:

$$A.F. = \frac{LD_{50} \text{ of Toxicant} \cdot \frac{1}{(xy+1)}}{\text{Experimental } LD_{50} \text{ of Combination}}$$

$X$ = The ratio of the % or weight of the synergist to the % or weight of the toxicant.

$Y$ = The ratio of the $LD_{50}$ of the toxicant to the $LD_{50}$ of the synergist.

The experimental $LD_{50}$ of the combination is in terms of the toxicant only.

The activating factor is, therefore, the ratio of the expected $LD_{50}$ of the combination divided by the experimental $LD_{50}$.

It is noted that when the observed response is greater than the expected, the Activating Factor is greater than one. This response is synergism.

TABLE II

| Insecticide* | HF ug 5,000 | BBA % .04 | SMC % 2.0 | CL % .1 | TBW % .5 | BAW % .2 |
|---|---|---|---|---|---|---|
| Insecticide* + Compound No. 1 | 30 | .005 | .03 | .005 | .005 | .005 |
| Compound No. 1 | >10,000 | >.25 | >.1 | >.1 | >.1 | >.1 |
| Activating Factor | 166.7 | 8.0 | 3.33 | >10.0 | >16.16 | >13.33 |
| Insecticide* + Compound No. 2 | 25 | .007 | .03 | .01 | .008 | .01 |
| Compound No. 2 | 10,000 | >.05 | .05 | >.1 | >.1 | >.1 |
| Activating Factor | 57.14 | 5.7 | 1.66 | >5.0 | >10.4 | >6.66 |
| Insecticide* + Compound No. 3 | 25.0 | .03 | >.05 | .01 | .03 | .02 |
| Compound No. 3 | >10,000 | >.05 | .05 | >.1 | >.1 | >.1 |
| Activating Factor | 200 | 1.33 | 1.0 | >5.0 | >2.78 | >3.33 |
| Insecticide* + Compound No. 4 | 20.0 | .007 | >.05 | .02 | .01 | .007 |
| Compound No. 4 | 8,000 | >.05 | >.1 | .05 | >.1 | >.1 |
| Activating Factor | 80.0 | 5.7 | 1.0 | 1.66 | >8.33 | >9.5 |
| Insecticide* + Compound No. 5 | 20 | .04 | .03 | .02 |  | .005 |
| Compound No. 5 | >10,000 | >.05 | .03 | >.1 |  | >.1 |
| Activating Factor | 250 | 1.0 | 1.0 | >2.5 |  | >13.33 |
| Insecticide* | 20 | .007 | >.1 | .007 |  | .006 |
| Compound No. 6 | >10,000 | >.05 | .1 | .05 |  | >.1 |
| Activating Factor | 250 | 5.7 | 1.0 | 4.76 |  | >11.11 |
| Insecticide* + Compound No. 7 | 20 | .007 | .03 | .1 |  | .006 |
| Compound No. 7 | >10,000 | >.05 | .05 | >.1 |  | >.1 |
| Activating Factor | 250 | >.05 | .05 | >.1 |  | >11.11 |
| Insecticide* + Compound No. 8 | 30 | .002 | .05 | .05 |  | .006 |
| Compound No. 8 | 10,000 | >.05 | >.05 | .1 |  | >.1 |
| Activating Factor | 47.6 | 20 | 1.0 | 1.0 |  | 11.11 |
| Insecticide* + Compound No. 9 | 40 | .002 | .05 | .03 |  | .007 |
| Compound No. 9 | >10,000 | >.05 | .05 | >.1 |  | .07 |
| Activating Factor | 125 | 20.0 | 1.0 | >1.66 |  | 9.5 |
| Insecticide* + Compound No. 10 | 80 | .007 | >.1 | >.05 |  | .009 |
| Compound No. 10 | 10,000 | >.05 | >.1 | >.1 |  | >.1 |
| Activating Factor | 47.6 | 7.14 | 1.10 | 1.0 |  | 7.41 |
| Insecticide* + Compound No. 11 | 40 | .008 | >.1 | .03 |  | .008 |
| Compound No. 11 | 6,000 | .05 | >.1 | .03 |  | >.1 |
| Activating Factor | 24.2 | 5.0 | 1.0 | 1.0 |  | >8.33 |
| Insecticide* + Compound No. 12 | >100 | .003 | .1 | .03 |  | .008 |
| Compound No. 12 | >10,000 | >.05 | >.1 | >.1 |  | >.1 |
| Activating |  |  |  |  |  |  |

TABLE II-continued

| Insecticide* | HF ug 5,000 | BBA % .04 | SMC % 2.0 | CL % .1 | TBW % .5 | BAW % .2 |
|---|---|---|---|---|---|---|
| Factor | ~1.0 | 13.33 | 1.0 | >1.66 | | >8.33 |
| Insecticide* + Compound No. 13 | >100 | .01 | >.05 | .003 | | .02 |
| Compound No. 13 | >10,000 | >.05 | >.05 | >.1 | | >.1 |
| Activating Factor | ~1.0 | 4.0 | 1.0 | >16.67 | | >3.33 |
| Insecticide* + Compound No. 14 | 30 | .008 | — | .01 | | .02 |
| Compound No. 14 | 11,000 | >.05 | >.05 | >.1 | | >.1 |
| Activating Factor | 36.46 | 5.0 | | >5.0 | | >3.33 |
| Insecticide* + Compound No. 15 | 50 | .003 | >.05 | .02 | | .05 |
| Compound No. 15 | 710,000 | >.05 | >.05 | >.1 | | >.1 |
| Activating Factor | 100 | 13.33 | 1.0 | >2.5 | | >1.33 |
| Insecticide* + Compound No. 16 | 40 | .005 | >.1 | .006 | | .007 |
| Compound No. 16 | 2,000 | >.05 | >.1 | .03 | | .1 |
| Activating Factor | 9.26 | 8.0 | 1.0 | 3.84 | | >9.5 |
| Insecticide* + Compound No. 17 | 30 | .008 | .05 | .02 | | .05 |
| Compound No. 17 | 2,000 | >.05 | >.1 | .1 | | >.1 |
| Activating Factor | 12.34 | 5.0 | >2.0 | 2.5 | | >1.33 |
| Insecticide* + Compound No. 18 | 30 | .007 | .05 | .03 | .1 | .007 |
| Compound No. 18 | 5,000 | >.05 | .05 | >.1 | >.1 | .1 |
| Activating Factor | 27.7 | 5.7 | 1.0 | >1.66 | >1.0 | 9.5 |
| Insecticide* + Compound No. 19 | 25 | .02 | >.05 | .02 | >.1 | .06 |
| Compound No. 19 | 2,500 | >.05 | >.05 | >.1 | >.1 | >.1 |
| Activating Factor | 18.18 | 2.0 | 1.0 | >2.5 | ~1.0 | >1.111 |
| Insecticide* + Compound No. 20 | 40 | .01 | >.05 | .02 | .08 | .008 |
| Compound No. 20 | 10,000 | >.05 | >.05 | .09 | >.1 | >.1 |
| Activating Factor | 35.7 | 4.0 | 1.0 | 2.37 | >1.25 | >8.33 |
| Insecticide* + Compound No. 21 | >100 | .005 | >.05 | .003 | .07 | .02 |
| Compound No. 21 | >10,000 | >.05 | >.05 | >.1 | >.1 | >.1 |
| Activating Factor | 1.0 | 8.0 | 1.0 | >16.67 | >1.42 | >3.33 |
| Insecticide* + Compound No. 22 | 20 | .003 | .01 | .005 | .005 | .005 |
| Compound No. 22 | 7,000 | >.25 | .07 | .1 | >.1 | .1 |
| Activating Factor | 54.7 | 13.33 | 7.0 | 10.0 | >16.67 | 13.33 |
| Insecticide* + Compound No. 23 | 35.0 | .01 | .01 | .01 | <.003 | .008 |
| Compound No. 23 | 10,000 | >.05 | .01 | .03 | <.03 | .06 |
| Activating Factor | 40.8 | 4.0 | 1.0 | 1.0 | — | 5.77 |
| Insecticide* + Compound No. 24 | 40 | .03 | .05 | .01 | .02 | .008 |
| Compound No. 24 | >10,000 | >.05 | .05 | .03 | .09 | >.1 |
| Activating Factor | 125 | 1.33 | 1.0 | 2.3 | 3.8 | >8.33 |
| Insecticide* + Compound No. 25 | 80 | .003 | .03 | .05 | .02 | .02 |
| Compound No. 25 | >10,000 | >.05 | .1 | .05 | .1 | >.1 |
| Activating Factor | 62.5 | 13.33 | 3.33 | 1.0 | 4.1 | >3.33 |
| Insecticide* + Compound No. 26 | 30.0 | .02 | .05 | .02 | .02 | .007 |
| Compound No. 26 | >10,000 | >.05 | >.05 | >.1 | .1 | >.1 |
| Activating Factor | 166.66 | 2.0 | >1.0 | 2.5 | 4.1 | >9.5 |
| Insecticide* + Compound No. 27 | 30 | .02 | .03 | .02 | .02 | .007 |
| Compound No. 27 | 9,000 | >.05 | .03 | >.1 | >.1 | .08 |
| Activating Factor | 44.12 | 2.0 | 1.0 | 5.0 | >4.167 | 8.16 |
| Insecticide* + Compound No. 28 | 50 | .01 | .03 | .005 | .009 | .009 |
| Compound No. 28 | 9,000 | >.05 | .03 | .1 | .1 | >.1 |
| Activating Factor | 26.47 | 4.0 | 1.0 | 10.0 | 9.26 | 7.41 |
| Insecticide* + Compound No. 29 | 10 | .003 | >.1 | .007 | .02 | .01 |
| Compound No. 29 | 2,000 | >.05 | >.1 | >.1 | >.1 | >.1 |
| Activating Factor | 9.26 | 13.33 | 1.0 | >7.14 | >4.167 | >6.66 |
| Insecticide* + Compound No. 30 | 80 | .01 | .05 | .02 | .005 | .02 |
| Compound No. 30 | >10,000 | >.05 | >.05 | >.1 | >.1 | >.1 |

TABLE II-continued

| Insecticide* | HF ug 5,000 | BBA % .04 | SMC % 2.0 | CL % .1 | TBW % .5 | BAW % .2 |
|---|---|---|---|---|---|---|
| Activating Factor | 62.5 | 4.0 | — | >2.5 | >16.67 | >3.33 |
| Insecticide* + Compound No. 31 | 10 | .01 | >.05 | .02 | >.003 | .02 |
| Compound No. 31 | 7,000 | >.05 | >.05 | >.1 | .1 | >.1 |
| Activating Factor | 109.4 | 4.0 | — | >2.5 | >27.8 | >3.33 |
| Insecticide* + Compound No. 32 | 30 | .01 | .05 | >.1 | .07 | .009 |
| Compound No. 32 | >10,000 | >.05 | >.05 | >.1 | >.1 | >.1 |
| Activating Factor | 166.66 | 4.0 | — | — | >1.2 | >7.4 |
| Insecticide* + Compound No. 33 | 35 | .01 | >.05 | .02 | >.1 | .02 |
| Compound No. 33 | >10,000 | >.05 | >.05 | >.1 | >.1 | >.1 |
| Activating Factor | 142.86 | 4.0 | — | >2.5 | — | >3.33 |
| Insecticide* + Compound No. 34 | 25 | .01 | >.05 | .03 | .003 | .02 |
| Compound No. 34 | >710,000 | >.05 | >.05 | >.1 | >.1 | >.1 |
| Activating Factor | 200 | 4.0 | — | >1.66 | >27.8 | >9.5 |
| Insecticide* + Compound No. 35 | 30 | .008 | >.05 | .02 | <.003 | .01 |
| Compound No. 35 | >10,000 | >.05 | >.05 | .09 | >.1 | >.1 |
| Activating Factor | 166.67 | 5.0 | — | 2.37 | >27.8 | >6.66 |
| Insecticide* + Compound No. 36 | 60 | .008 | .05 | .006 | .007 | .007 |
| Compound No. 36 | >10,000 | >.05 | >.05 | .06 | <.03 | .08 |
| Activating Factor | 83.33 | 5.0 | — | 6.25 | <4.0 | 8.16 |
| Insecticide* + Compound No. 37 | 40 | .03 | >.05 | .02 | .03 | .009 |
| Compound No. 37 | >10,000 | >.05 | >.05 | .09 | .03 | >.1 |
| Activating Factor | 125 | 1.33 | — | 2.37 | 1.0 | 7.41 |
| Insecticide* + Compound No. 38 | 30 | — | >.05 | .008 | .005 | .008 |
| Compound No. 38 | 7,000 | >.05 | >.05 | >.1 | .06 | >.1 |
| Activating Factor | 36.46 | — | — | >6.25 | 10.0 | >8.33 |
| Insecticide* + Compound No. 39 | 40 | — | >.05 | .02 | <.003 | .005 |
| Compound No. 39 | 3,000 | >.05 | >.05 | >.1 | .07 | >.1 |
| Activating Factor | 13.4 | — | — | 2.5 | 2.5 | >13.33 |
| Insecticide* + Compound No. 40 | >100 | — | >.05 | .009 | .07 | .009 |
| Compound No. 40 | 7,000 | .05 | >.05 | >.1 | .1 | >.1 |
| Activating Factor | >10.94 | — | — | >5.55 | 1.2 | >7.40 |
| Insecticide* + Compound No. 41 | 2.5 | — | 0.03 | 0.007 | .02 | — |
| Compound No. 41 | >100 | — | >0.1 | 0.07 | >0.1 | — |
| Activating Factor | >1.2 | — | >3.2 | 5.9 | >4.1 | — |
| Insecticide* + Compound No. 42 | 2.5 | — | 0.02 | 0.007 | 0.02 | — |
| Compound No. 42 | >100 | — | 0.07 | 0.03 | 0.1 | — |
| Activating Factor | >1.2 | — | >3.4 | 3.3 | 4.1 | — |
| Insecticide* + Compound No. 43 | 2.5 | — | 0.02 | 0.003 | 0.07 | — |
| Compound No. 43 | >100 | — | 0.07 | 0.03 | >0.1 | — |
| Activating Factor | >1.2 | — | >3.4 | 7.7 | >1.2 | — |
| Insecticide* + Compound No. 44 | 1.5 | — | 0.02 | 0.007 | 0.02 | — |
| Compound No. 44 | >100 | — | >0.1 | 0.07 | >0.1 | — |
| Activating Factor | >2.0 | — | >4.7 | 2.2 | >4.1 | — |

*Insecticide = N-(mercaptomethyl) phthalimide-S-(O,O-dimethyl-phosphorodithioate).

The compositions of this invention are generally embodied into a form suitable for convenient application. For example, the compositions can be embodied into pesticidal formulations which are provided in the form of emulsions, suspensions, solutions, dusts, and aerosol sprays. In general, such formulations will contain, in addition to the active compound, the adjuvants which are found normally in pesticide preparations. In these formulations, the active compounds of this invention can be employed as the sole pesticide component or they can be used in admixture with other compounds having similar utility. The pesticide formulations of this invention can contain, as adjuvants, organic solvents, such as sesame oil, xylene range solvents, heavy petroleum, etc.; water; emulsifying agents; surface active agents; talc; pyrophyllite, diatomite; gypsum; clays; propellants, such as dichlorodifluoromethane, etc. If desired, however, the active compositions can be applied directly to feedstuffs, seeds, etc., upon which the pests feed. Then applied in such a manner, it will be advantageous to use a composition which is not volatile. In connection with the activity of the presently disclosed pesticidal compositions, it should be fully understood that it is not necessary that they be active as such. The purposes of this invention will be fully served if the composition is rendered active by external influences, such as light, or by some physiological action which occurs when the compound is ingested into the body of the pest.

The precise manner in which the pesticidal compositions of this invention are used in any particular instance will be readily apparent to a person skilled in the art. Generally, the active pesticide composition will be embodied in the form of a liquid composition; for example, an emulsion, suspension, or aerosol spray. While the concentration of the active pesticide composition in the present formulation can vary within rather wide limits, ordinarily, the pesticide composition will comprise not more than about 50.0% by weight of the formulation.

What is claimed is:

1. An insecticidally active composition comprising an insecticidally effective amount of an insecticide which is N-(mercaptomethyl) phthalimide-S-(O,O-dimethylphosphorodithioate) and an effective amount of an activator having the formula

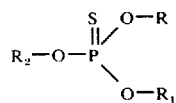

wherein R is selected from the group consisting of methyl, ethyl, n-propyl, i-propyl and i-butyl; $R_1$ is selected from the group consisting of methyl, ethyl, n-propyl, i-propyl, n-butyl and i-butyl and $R_2$ is selected from the group consisting of phenyl, substituted phenyl wherein said substituents are selected from the group consisting of methyl, ethyl, i-propyl, t-butyl, methoxy, ethoxy, and dimethylamino; phenalkyl and substituted phenalkyl wherein said substituents are selected from the group consisting of chlorine, methyl, i-propyl and methoxy, said activator being present in an amount ranging between 0.1 and 10.0 parts by weight per each part by weight insecticide and being effective to increase the activity of the insecticide.

2. The composition of claim 1 wherein R is —$CH_3$, $R_1$ is —$CH_3$ and $R_2$ is

3. The composition of claim 1, wherein R is —$CH_3$, and $R_2$ is

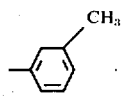

4. The composition of claim 1, wherein R is -$CH_3$, $R_1$ is -$CH_3$ and $R_2$ is

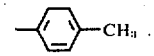

5. The composition of claim 1, wherein R is -$CH_3$, $R_1$ is -$CH_3$ and $R_2$ is

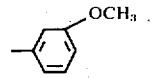

6. The composition of claim 1, wherein R is —$CH_3$, $R_1$ is —$CH_3$ and $R_2$ is

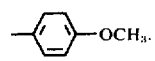

7. The composition of claim 1, wherein R is —$CH_3$, $R_1$ is —$CH_3$ and $R_2$ is

8. The composition of claim 1, wherein R is —$CH_3$, $R_1$ is —$CH_3$ and $R_2$ is

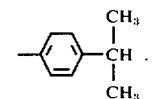

9. The composition of claim 1, wherein R is —$CH_3$, $R_1$ is —$CH_3$ and $R_2$ is

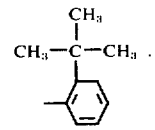

10. The composition of claim 1, wherein R is —$CH_3$, $R_1$ is —$CH_3$ and $R_2$ is

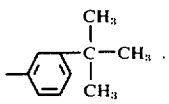

11. The composition of claim 1, wherein R is —$CH_3$, $R_1$ is —$CH_3$ and $R_2$ is

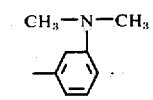

12. The composition of claim 1, wherein R is —$CH_3$, $R_1$ is —$CH_3$ and $R_2$ is

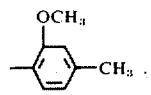

13. The composition of claim 1, wherein R is —CH$_3$, R$_1$ is —CH$_3$ and R$_2$ is

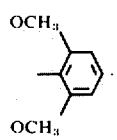

14. The composition of claim 1, wherein R is —CH$_3$, R$_1$ is —CH$_3$ and R$_2$ is

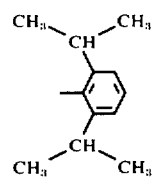

15. The composition of claim 1, wherein R is —CH$_3$, R$_1$ is —CH$_3$ and R$_2$ is

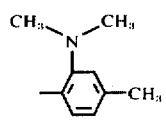

16. The composition of claim 1, wherein R is

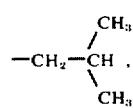

R$_1$ is

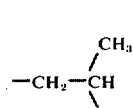

and R$_2$ is

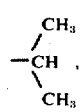

17. The composition of claim 1, wherein R is

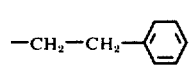

R$_1$ is

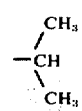

and R$_2$ is

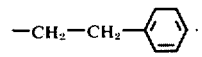

18. The composition of claim 1, wherein R is —CH$_3$, R$_1$ is —CH$_3$ and R$_2$ is

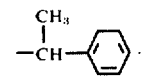

19. The composition of claim 1, wherein R is —CH$_3$, R$_1$ is —CH$_3$ and R$_2$ is

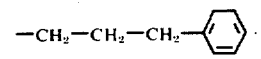

20. The composition of claim 1, wherein R is —CH$_3$, R$_1$ is —CH$_3$ and R$_2$ is

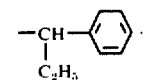

21. The composition of claim 1, wherein R is —CH$_3$, R$_1$ is —CH$_3$ and R$_2$ is

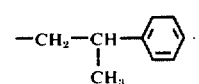

22. The composition of claim 1, wherein R is —CH$_3$, R$_1$ is —CH$_3$ and R$_2$ is

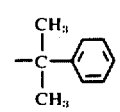

23. The composition of claim 1, wherein R is —C$_2$H$_5$, R$_1$ is C$_2$H$_5$ and R$_2$ is

24. The composition of claim 1, wherein R is —C$_3$H$_7$, R$_1$ is —C$_3$H$_7$ and R$_2$ is

25. The composition of claim 1, wherein R is

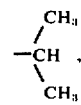

R$_1$ is

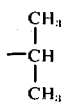

and $R_2$ is

26. The composition of claim 1, wherein R is

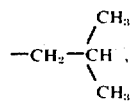

$R_1$ is

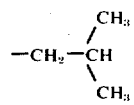

and $R_2$ is

27. The composition of claim 1, wherein R is $-CH_3$, $R_1$ is $-CH_3$ and $R_2$ is

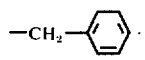

28. The composition of claim 1, wherein R is $-CH_3$, $R_1$ is $-CH_3$ and $R_2$ is

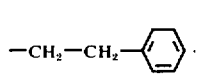

29. The composition of claim 1, wherein R is $-C_2H_5$, $R_1$ is $-C_2H_5$ and $R_2$ is

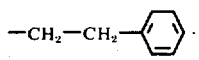

30. The composition of claim 1, wherein R is $-C_3H_7$, $R_1$ is $-C_3H_7$ and $R_2$ is

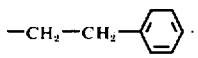

31. The composition of claim 1, wherein R is $-C_2H_5$, $R_1$ is $-C_2H_5$ and $R_2$ is

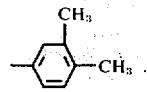

32. The composition of claim 1, wherein R is $-C_2H_5$, $R_1$ is $-C_2H_5$ and $R_2$ is

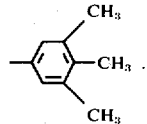

33. The composition of claim 1, wherein R is $-C_2H_5$, $R_1$ is $-C_2H_5$ and $R_2$ is

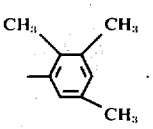

34. The composition of claim 1, wherein R is $-C_2H_5$, $R_1$ is $-C_2H_5$ and $R_2$ is

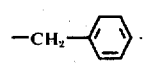

35. The composition of claim 1, wherein R is $-C_2H_5$, $R_1$ is $-C_2H_5$ and $R_2$ is

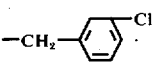

36. The composition of claim 1, wherein R is $-C_2H_5$, $R_1$ is $-C_2H_5$ and $R_2$ is

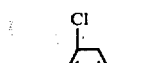

37. The composition of claim 1, wherein R is $-C_{25}$, $R_1$ is $-C_2H_5$ and $R_2$ is

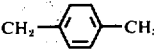

38. The composition of claim 1, wherein R is $-C_2H_5$, $R_1$ is $-C_2H_5$ and $R_2$ is 39. The composition of claim 1, wherein R is $-C_2H_5$, $R_1$ is $-C_2H_5$ and $R_2$ is

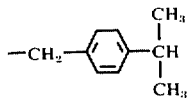

40. The composition of claim 1, wherein R is —C₂H₅, R₁ is —C₂H₅ and R₂ is

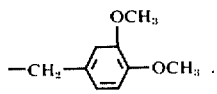

41. An insecticidally active composition comprising an insecticidally effective amount of an insecticide which is N-(mercaptomethyl) phthalimide-S-(O,O-dimethylphosphorodithioate) and an effective amount of an activator having the formula

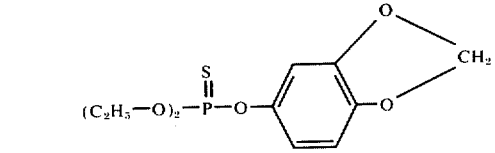

said activator being present in an amount ranging between 0.1 and 10.0 parts by weight per each part by weight insecticide and being effective to increase the activity of the insecticide.

* * * * *